США008568458B2

(12) United States Patent
Matthis et al.

(10) Patent No.: US 8,568,458 B2
(45) Date of Patent: Oct. 29, 2013

(54) BONE ANCHORING DEVICE

(75) Inventors: Wilfried Matthis, Weisweil (DE); Lutz Biedermann, VS-Villingen (DE); Stefan Freudiger, Bremgarten (CH)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 778 days.

(21) Appl. No.: 11/854,508

(22) Filed: Sep. 12, 2007

(65) Prior Publication Data

US 2008/0114404 A1  May 15, 2008

Related U.S. Application Data

(60) Provisional application No. 60/825,841, filed on Sep. 15, 2006.

(30) Foreign Application Priority Data

Sep. 15, 2006  (EP) ..................................... 06019341

(51) Int. Cl.
*A61B 17/88* (2006.01)

(52) U.S. Cl.
USPC ........................................................ 606/264

(58) Field of Classification Search
USPC ......... 606/246, 265–268, 270, 272, 277–279, 606/295, 301, 302, 304–308, 328, 311, 312, 606/315, 317
See application file for complete search history.

(56) References Cited

U.S. PATENT DOCUMENTS

| 5,005,562 A | 4/1991 | Cotrel |
| 5,257,993 A | 11/1993 | Asher et al. |
| 5,261,912 A | 11/1993 | Frigg |
| 5,282,863 A | 2/1994 | Burton |

(Continued)

FOREIGN PATENT DOCUMENTS

| EP | 0 348 272 A1 | 12/1989 |
| EP | 1 364 622 A2 | 11/2003 |

(Continued)

OTHER PUBLICATIONS

European Search Report dated Feb. 22, 2007 for European Application No. 06019341.4-1526, Date of Completion Feb. 7, 2007, Place of Search Berlin, (9 pages).

(Continued)

*Primary Examiner* — Mary Hoffman
*Assistant Examiner* — Tara Carter
(74) *Attorney, Agent, or Firm* — Christie, Parker & Hale, LLP

(57) ABSTRACT

A bone anchoring device is provided that includes an anchoring element with a shank to be anchored in a bone or a vertebra, a connection element for connecting at least two anchoring elements, the connection element being made of an elastic material, a receiving part being connected to the shank for receiving the connection element and connecting the connection element to the shank, a seat for the connection element the seat being provided in the receiving part, and a locking element being engageable with the receiving part for fixation of the connection element in the seat. At least the portion of the connection element which is received in the recess has a substantially smooth-surface. The locking element has an engagement structure which contacts the surface of the connection element in such a way that a form-fit connection is provided.

21 Claims, 5 Drawing Sheets

(56) References Cited

U.S. PATENT DOCUMENTS

| | | | |
|---|---|---|---|
| 5,360,431 | A | 11/1994 | Puno et al. |
| 5,520,689 | A | 5/1996 | Schläpfer et al. |
| 5,540,688 | A | 7/1996 | Navas |
| 5,658,284 | A | 8/1997 | Sebastian et al. |
| 6,077,262 | A | 6/2000 | Schläpfer et al. |
| 6,117,137 | A | 9/2000 | Halm et al. |
| 6,224,598 | B1 | 5/2001 | Jackson |
| 6,478,797 | B1 | 11/2002 | Paul |
| 6,565,565 | B1 | 5/2003 | Yuan et al. |
| 6,652,526 | B1 | 11/2003 | Arafiles |
| 6,783,527 | B2 * | 8/2004 | Drewry et al. ............ 606/254 |
| 6,793,657 | B2 | 9/2004 | Lee et al. |
| 6,896,677 | B1 | 5/2005 | Lin |
| 7,731,749 | B2 | 6/2010 | Biedermann et al. |
| 8,282,672 | B2 | 10/2012 | Freudiger |
| 2001/0020168 | A1 | 9/2001 | Hermann et al. |
| 2001/0023350 | A1 | 9/2001 | Choi |
| 2003/0083657 | A1 | 5/2003 | Drewry et al. |
| 2003/0125742 | A1 | 7/2003 | Yuan et al. |
| 2003/0220642 | A1 | 11/2003 | Freudiger |
| 2004/0039383 | A1 | 2/2004 | Jackson |
| 2004/0138660 | A1 | 7/2004 | Serhan |
| 2004/0172025 | A1 | 9/2004 | Drewry et al. |
| 2005/0096659 | A1 | 5/2005 | Freudiger |
| 2005/0203518 | A1 | 9/2005 | Biedermann et al. |
| 2007/0042633 | A1 | 2/2007 | Frigg et al. |
| 2007/0093820 | A1 | 4/2007 | Freudiger |
| 2007/0093821 | A1 | 4/2007 | Freudiger |
| 2007/0161999 | A1 | 7/2007 | Biedermann et al. |
| 2010/0286731 | A1 | 11/2010 | Biedermann et al. |
| 2013/0079824 | A1 | 3/2013 | Freudiger |

FOREIGN PATENT DOCUMENTS

| | | |
|---|---|---|
| EP | 1 527 742 A1 | 5/2005 |
| JP | 11-502437 | 3/1999 |
| JP | 2001-258894 | 9/2001 |
| JP | 2002-320622 | 11/2002 |
| JP | 2005-169071 | 6/2005 |
| JP | 2006-521903 A | 9/2006 |
| JP | 2007-136196 | 6/2007 |
| WO | WO 96/28118 | 9/1996 |
| WO | WO 2004/089244 A2 | 10/2004 |
| WO | WO 2005/084566 A1 | 9/2005 |
| WO | WO 2005/122929 A1 | 12/2005 |

OTHER PUBLICATIONS

English Translation of Submission of the Facts and Circumstances and Grounds of Opposition against European Patent No. 1 900 334, Application No. 06019341.4 of Patent Proprietor Biedermann Motech GmbH, 7 pages.
Current claims for U.S. Appl. No. 11/512,461 (6 sheets).
Current claims for U.S. Appl. No. 12/789,162 (3 sheets).
Current claims for U.S. Appl. No. 11/520,286 (6 sheets).
English translation of Japanese Office action for application No. JP 2007-236712, dated Jun. 12, 2012, 2 pages.
OA dated Oct. 1, 2008 for U.S. Appl. No. 11/512,461 (8 sheets).
OA dated May 22, 2009 for U.S. Appl. No. 11/512,461 (8 sheets).
OA dated Jan. 20, 2010 for U.S. Appl. No. 11/512,461 (9 sheets).
OA dated Aug. 2, 2010 for U.S. Appl. No. 11/512,461 (10 sheets).
OA dated Dec. 17, 2010 for U.S. Appl. No. 11/512,461 (2 sheets).
OA dated Jun. 21, 2011 for U.S. Appl. No. 11/512,461 (7 sheets).
OA dated May 11, 2011 for U.S. Appl. No. 12/789,162 (9 sheets).
OA dated Jan. 4, 2012 for U.S. Appl. No. 12/789,162 (9 sheets).
OA dated Dec. 22, 2008 for U.S. Appl. No. 11/520,286 (10 sheets).
OA dated May 1, 2009 for U.S. Appl. No. 11/520,286 (14 sheets).
OA dated Sep. 23, 2009 for U.S. Appl. No. 11/520,286 (10 sheets).
OA dated Apr. 9, 2010 for U.S. Appl. No. 11/520,286 (12 sheets).
OA dated Feb. 12, 2013 for U.S. Appl. No. 11/520,286 (11 sheets).
OA dated Apr. 25, 2013 for U.S. Appl. No. 13/596,888 (7 sheets).
Office action for U.S. Patent Application No. 11/520,286, dated Sep. 12, 2013, 14 sheets.
Office action dated Aug. 13, 2013 for U.S. Appl. No. 12/789,162, 12 pages.

\* cited by examiner

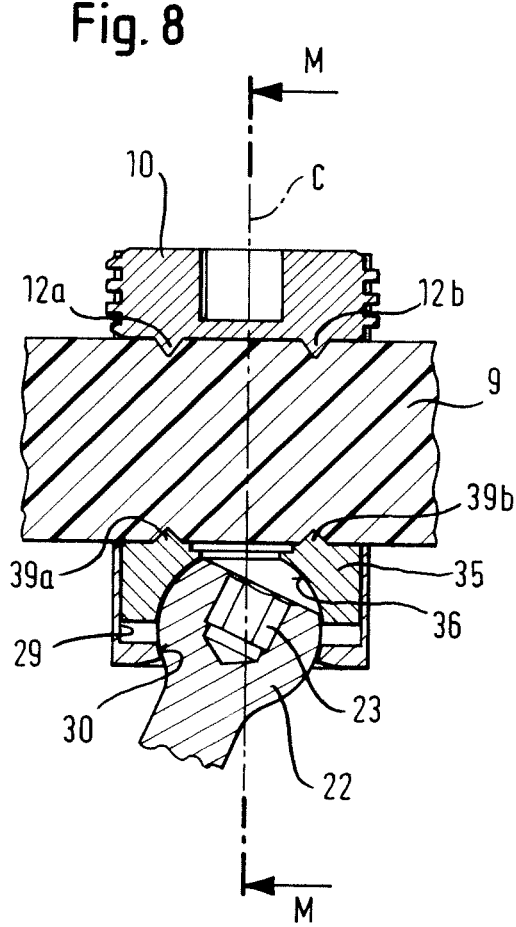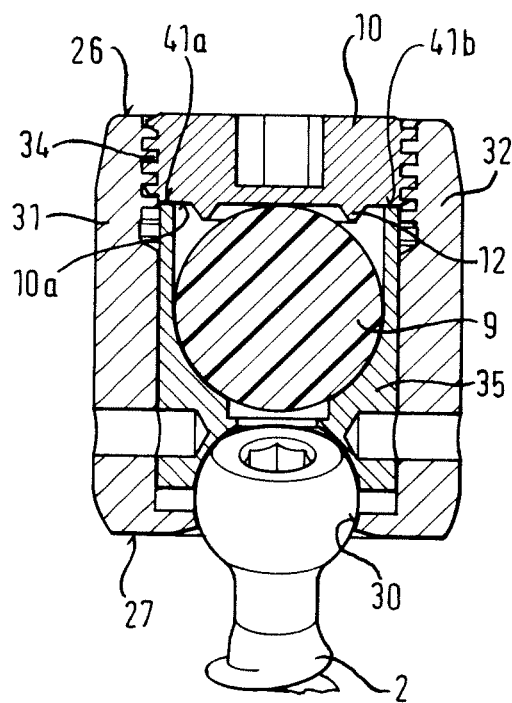

BONE ANCHORING DEVICE

CROSS-REFERENCE TO RELATED APPLICATIONS

The present application claims the benefit of U.S. Provisional Patent Application Ser. No. 60/825,841, filed Sep. 15, 2006, and claims priority from European Patent Application EP06019341.4, filed Sep. 15, 2006, the entire disclosures of which are incorporated herein by reference.

BACKGROUND

The present application generally relates to a bone anchoring device for the dynamic stabilization of bones, in particular for the dynamic stabilization of the spine, and in particular, to a bone anchoring element which can be connected with a flexible rod which has a smooth surface and which is made of an elastic material.

Bone anchoring devices comprising a bone screw and a flexible rod which is made of an elastic material are known from EP 1 364 622 A2 and EP 1 527 742 A1. The rod has a corrugated surface which cooperates with a rib structure provided on the bottom of the receiving part of the bone screw to form a form-fit connection. The bone anchoring device according to EP 1 527 742 A1 additionally comprises a closure element which has a rib structure engaging the corrugated surface of the rod. The positioning of the corrugated surfaces of the rod relative to the rib structure requires a precise insertion of the rod into the receiving part to avoid tilting. Furthermore, a continuous positioning is not possible. This makes the adjustment of the position of the rod relative to the receiving part difficult and time consuming.

US 2004/0138660 A1 discloses a locking cap assembly for locking a rigid rod to a receiving body of a bone screw. The locking cap assembly includes an inner and an outer locking element. The outer locking element is a nut-like member and the inner locking element is rotatably connected to the outer locking element. The inner locking element has on its side facing the rod a ring-shaped deformable contacting element which comes into contact with the rod. Upon tightening of the outer locking element, the deformable element is deformed which provides feed-back to the surgeon to allow him to determine whether the locking cap assembly is tightened to the required extent. In one example, the deformable element is a deformable metallic ring which becomes cold welded to the rod.

Based on the above, there is a need to provide a bone anchoring device which can be used with a flexible rod made of an elastic material and which has a convenient handling while simultaneously providing a safe locking.

SUMMARY OF THE INVENTION

In a bone anchoring device according to the disclosure, during tightening of the locking element the deformation of the elastic material of the rod can lead to an indirect or dynamic form-fit connection between the elastic rod, the receiving part and the locking element without harming the integral structure of the rod.

Since the rod has a smooth surface, continuous positioning of the rod is possible.

In the bone anchoring device according to the disclosure a flow of the material of the rod in a direction along the longitudinal axis of the rod is minimized.

The fixation of the rod is achieved with a small number of parts. Therefore, the handling of the bone anchoring device during surgery is facilitated without loss of reliability of the fixation.

Further features and advantages of the invention will become apparent and will be best understood by reference to the following detailed description of embodiments taken in conjunction with the accompanying drawings.

BRIEF DESCRIPTION OF THE DRAWINGS

FIG. 8 shows a portion of the bone fixation device according to FIG. 7 in an assembled state in a sectional view the section being taken along the rod axis.

FIG. 9 shows a sectional view of the bone anchoring device of FIG. 8 along the line M-M.

DETAILED DESCRIPTION OF THE INVENTION

Figure 1:
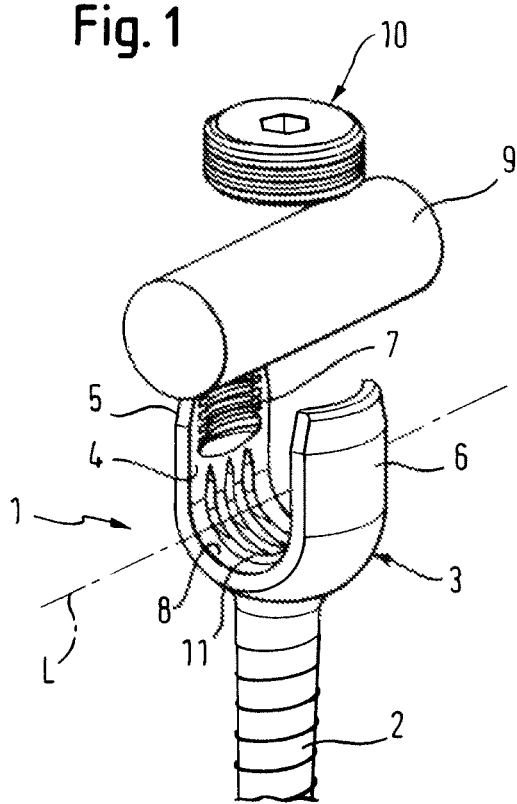
FIG. 1 shows a perspective exploded view of a first embodiment of the bone anchoring device.
Figure 3:
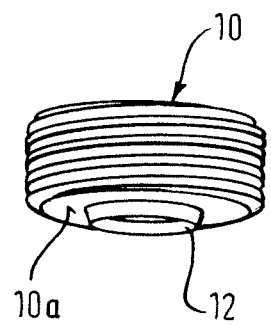
FIG. 3 shows a perspective view of the locking element of the bone anchoring device of FIG. 1.
Figure 2:
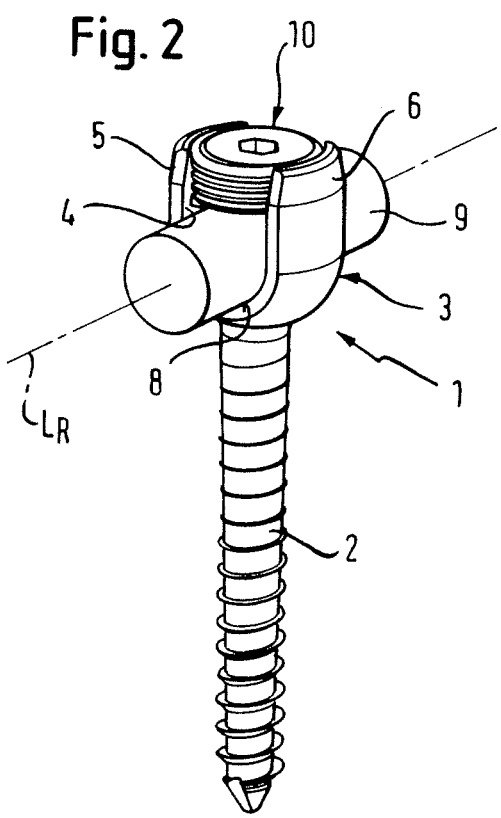
FIG. 2 shows the bone anchoring device of FIG. 1 in an assembled state.

As shown in FIGS. 1 to 4 the bone anchoring device according to a first embodiment comprises a bone anchoring element 1 in the form of a monoaxial bone screw having a shank 2 with a bone thread and a tip at one end and a receiving part 3 at the opposite end. The receiving part 3 is substantially cylindrically-shaped and comprises a substantially U-shaped recess 4 forming two free legs 5,6. An internal thread 7 is provided on the legs. The bottom of the U-shaped recess forms a seat 8 for receiving a rod 9. The rod 9 is used to connect several bone anchoring elements. To secure the rod 9 in the recess 4, a locking element in the form of an inner screw 10 is provided which can be screwed-in between the legs 5, 6.

Figure 4:
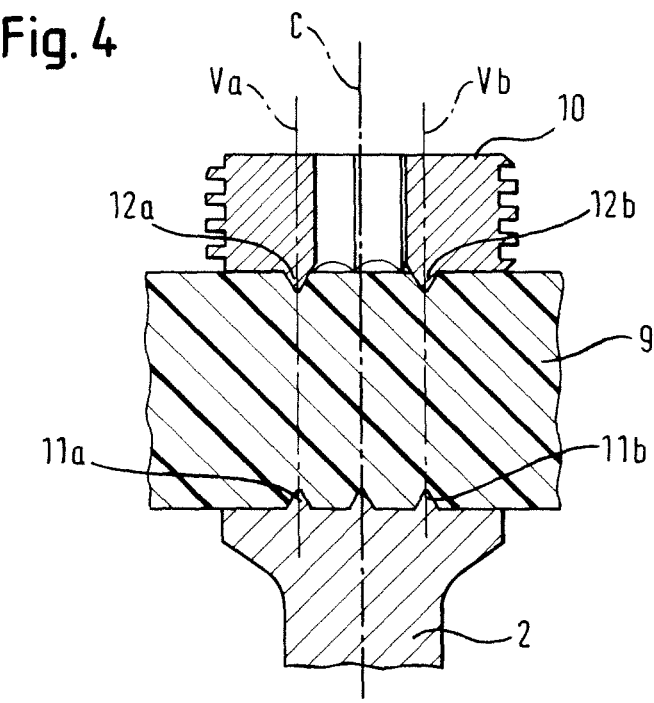
FIG. 4 shows a sectional view of a portion of the bone anchoring device of FIG. 1 and 2.

As can be seen in particular in FIGS. 1 and 4 a plurality of rib-like projections 11 are provided on the surface of the seat 8. The rib-like projections 11 extend in a direction perpendicular to the longitudinal axis L of the recess 4 and hence extend perpendicular to the longitudinal axis LR of the rod 9. In the embodiment shown the projections 11 have a substantially triangular cross-section with a rounded tip. The projections 11 have such a length that they form a U-shape corresponding to the seat 8. They end at a distance from the internal thread 7. Each or several of the rib-like projections 11 may run out on one or on either side in groove-like recesses which provide depressions in the surface of the seat. Alternatively, one or several depressions in the surface of the seat which adjoins one or several of the projections can be provided.

The rod 9 is made of an elastic flexible biocompatible material, preferably of plastics. For example, the rod 9 is made of an elastomer material on the basis of polycarbonate polyurethane or polycarbonateurethane (PCU). Hence, the rod shows elastic deformation under applied external loads.

The inner screw 10 which is to be screwed between the legs 5, 6 comprises at its side 10a facing the rod 9 a ring shaped projection 12 in form of an annular rib with a central cavity. As can be seen in particular in FIG. 4, the ring-shaped projection 12 has a cross-section which is similar to the cross-section of the rib-like projections 11 of the seat. When the ring-shaped projection 12 comes into contact with the rod 9, two contact areas 12a and 12b are provided where the ring-shaped projection presses onto the rod. The diameter of the ring-shaped projection 12 is such that the contact areas 12a, 12b and the contact areas 11a and 11b of the two outer rib-like projections are located on opposite sides of the surface of the rod 9 on a vertical line Va, Vb which is parallel to the central axis C of the receiving part 3, respectively.

The bone anchoring element 1 and the inner screw 10 are made of a biocompatible rigid material, preferably of a metal, such as titanium or a titanium alloy.

In use, first at least two bone anchoring elements 1 are screwed into adjacent vertebrae, for example into the pedicles of the vertebrae. Thereafter rod 9 is inserted into the receiving parts 3 until it is seated in the seat 8. Thereafter the rod is locked in its position by screwing-in the inner screw 10. If the inner screw 10 is not yet tightened, the position of the rod can still be adjusted in a stepless manner, since the rod has a smooth surface. After adjusting the position of the rod the inner screw 10 is tightened until the ring-shaped projection 12 comes into contact with the surface of the rod. As can be seen in FIG. 4 the opposite portions 12a and 12b of the ring-shaped projection are pressed down on the surface of the rod. Similarly the rib-like projections 11 are pressing on the surface of the rod from below. The projections do not harm the integrity of the surface of the rod. The rod begins to flow under applied pressure. This material flow results in an indirect form-fit connection. The combination of direct frictional forces and indirect form-fit forces holds the rod in place.

The diameter of the ring-shaped projection 12 can be equal or larger than the distance between the outmost rib-like projections 11.

Figure 5A:
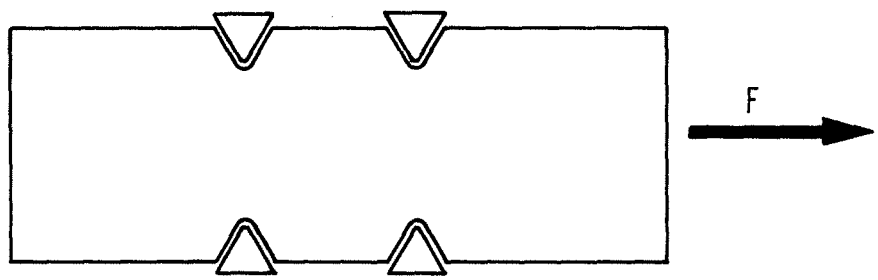
FIG. 5a shows a schematic view of the fixation mechanism of the bone anchoring device according to the invention.

As can be seen in FIG. 5a, one arrangement of the engagement structure formed by the projections of the seat and the engagement structure formed by the projection on the locking element at corresponding locations on opposite surface portions of the rod provides a form-fit connection which is resistant to a force F acting in the longitudinal direction of the rod 9.

Figure 5B:
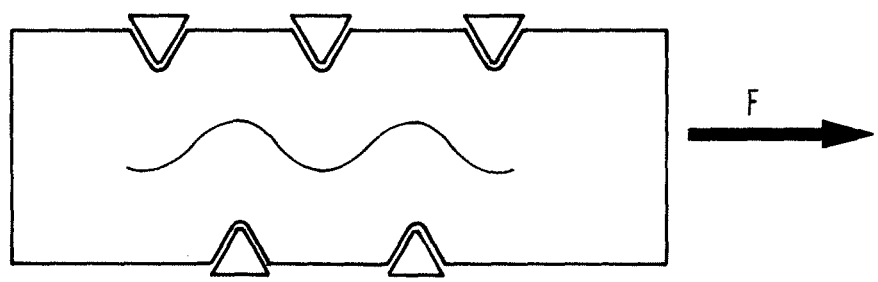
FIG. 5b shows a schematic view of another fixation mechanism.
Figure 6:
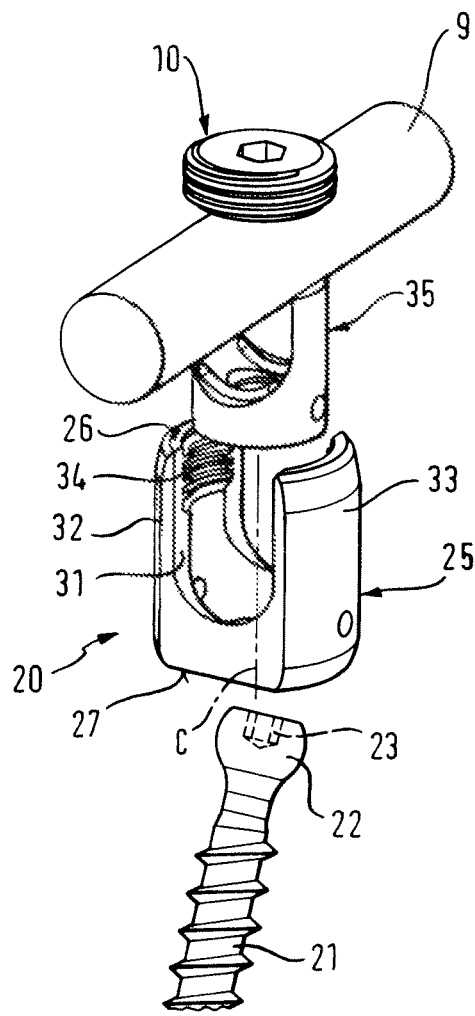
FIG. 6 shows an perspective exploded view of a bone anchoring device according a second embodiment.
Figure 7:
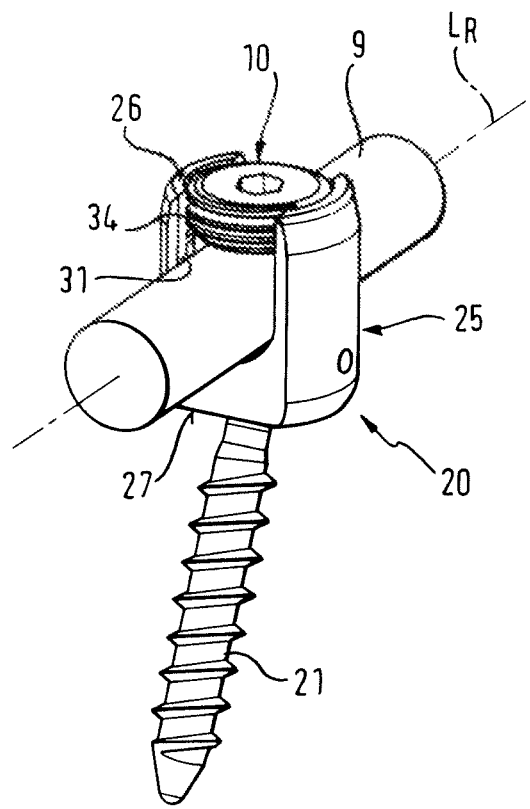
FIG. 7 shows a perspective view of the bone anchoring device shown in FIG. 6 in an assembled state.
Figure 10:
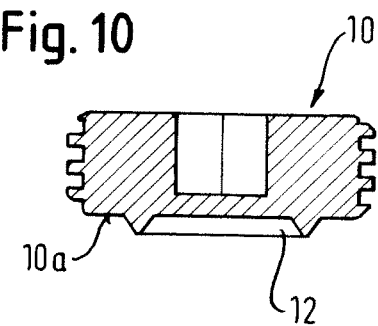
FIG. 10 shows a sectional view of the locking element of the second embodiment.
Figure 11:
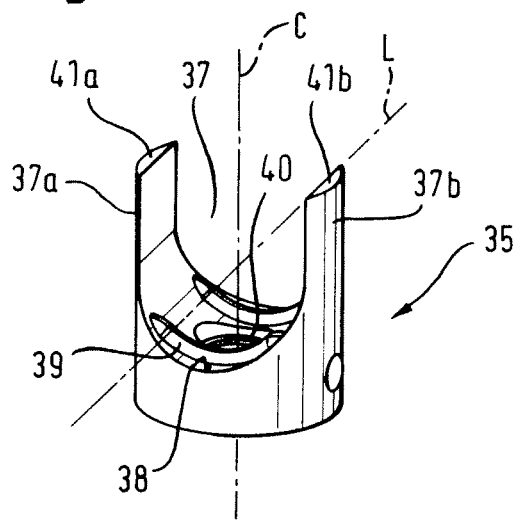
FIG. 11 shows a perspective view of the pressure element of the bone anchoring device according to the second embodiment.
Figure 12:
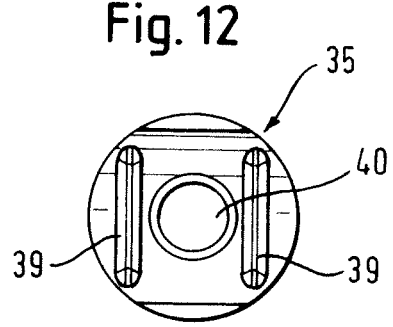
FIG. 12 shows a top view of the pressure element shown in FIG. 11.
Figure 13:
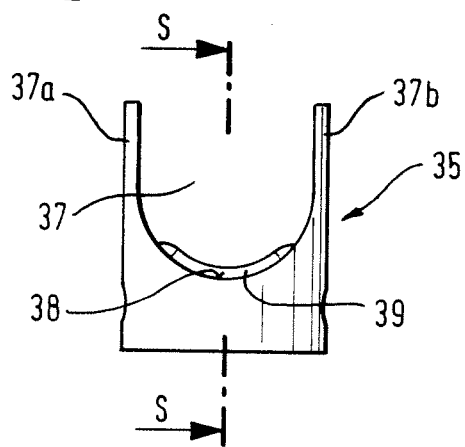
FIG. 13 shows a side view of the pressure element shown in FIG. 11.
Figure 14:
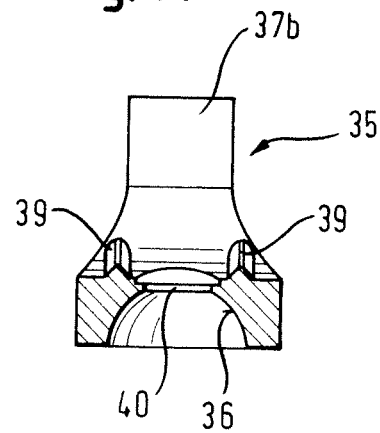
FIG. 14 shows a sectional view of the pressure element shown in FIG. 11 along the line S-S in FIG. 13.

An alternating arrangement of the projections of the seat and that of the locking element with respect to the rod as shown in FIG. 5b, also leads to an indirect form-fit connection as described above, which, however, is less resistant to a force F acting in the axial direction of the rod. In case of a large force F, the connection shown in FIG. 5b cannot prohibit a wavy-like movement of the rod and hence provides less fixation of the rod.

The ring-shaped projection of the inner screw makes it possible that the engagement structure is provided at the locking element itself instead of using a filling piece or pressure piece.

FIG. 6 to 14 show a second embodiment of the bone anchoring device. The bone anchoring device comprises a bone anchoring element 20 in the form of a polyaxial bone screw having a screw element with a shank 21 with a bone thread, a tip at one end and a spherical head 22 at the opposite end. A recess 23 for engagement with the screwing-in tool is provided at the side of the head 22 which is opposite to the shank.

The bone anchoring element 20 further comprises a receiving part 25 which has a first end 26 and a second end 27 opposite to the first end and a central axis C intersecting the plane of the first end and the second end. Coaxially with the central axis C a bore 29 is provided which extends from the first end to a predetermined distance from the second end. At the second end 27 an opening 30 is provided the diameter of which is smaller than the diameter of the bore 29. The head 22 is pivotably held in the receiving part 25 with the shank extending through the opening 30.

The receiving part 25 further has a substantially U-shaped recess 31 which starts at the first end 26 and extends in the direction of the second end 27. By means of the U-shaped recess two free legs 32,33 are formed which have an internal thread 34.

A pressure element 35 is provided which has a substantially cylindrical construction with an outer diameter which is only slightly smaller than the inner diameter of the bore 29 to allow the pressure element 35 to be introduced into the bore 29 of the receiving part and to be moved in the axial direction. On its lower side facing towards the second end 27 the pressure element 35 comprises a spherical recess 36 the radius of which corresponds to the radius of the spherical thread 22 of the screw element. On the opposite side pressure the element 35 comprises a U-shaped recess 37 extending transversely to the central axis C. The lateral diameter of this recess is selected such that the rod 9 which is to be received in the receiving part 3 can be inserted into the recess 37 and guided laterally therein. The depth of the U-shaped recess 37 is selected such that in an assembled state when the rod is placed into the U-shaped recess 37, legs 37a, 37b of the recess extend up to the upper surface of the rod. Preferably, the depth of the recess 37 is equal to the diameter of the rod 9. The lateral diameter of the recess in the area of the ribs and/or the depth of the recess 37 can be slightly larger than the diameter of the rod to allow local plastic flow of the material of the rod.

The bottom 38 of the U-shaped recess of the pressure element 35 forms a seat for the rod 9. Similar to the first embodiment a plurality of rib-like projections 39 are provided on the surface of the seat 38. In the embodiment shown, there are two rib-like projections 39, extending in a direction transversely to the longitudinal axis 1 of the U-shaped recess 37 and, therefore, transversely to the longitudinal axis LR of the rod 9. Furthermore, the pressure element comprises a coaxial bore 40 to allow access to the recess 23 of the head 22 with a screwing-in tool.

The locking element is the inner screw 10 as in the first embodiment, which has the ring-shaped projection 12 on its side 10a facing the rod 9. The dimensions of the ring-shaped projection 12 is such that, as shown in FIG. 8, the contact areas 12a and 12b of the ring-shaped projection 12 with the rod are located at positions corresponding to the contact areas 39a, 39b of the rib-like projections of the pressure element on opposite sides of the rod.

The dimensions of the pressure element 35 and the inner screw 10 are such that in the assembled state the lower side 10a of the inner screw rests on the upper end surface 41a, 41b of the legs of the pressure element. The dimensions of the projections 39 of the pressure element and the ring-shaped projection 12 of the inner screw are such that safe fixation by means of a press-fit with indirect form-fit is achieved without harming the integrity of the surface of the rod.

In use, the bone anchoring element 20 is preassembled, i.e. the bone screw is pivotably held in the receiving part and the pressure element is inserted and slightly held in a position in which its U-shaped recess is aligned with the U-shaped recess of the receiving part. The bone anchoring element is screwed into the bone and the angular position of the receiving part relative to the bone screw is adjusted. The rod 9 is inserted and the inner screw 10 tightened down until it clamps the rod. The function of the clamping is the same as in the first embodiment. When tightening the inner screw presses onto the upper end surface 41a, 41b of the pressure element and thus presses down the pressure element onto the head 22 to lock the angular position of the head in the receiving part.

Since the lower side 10a of the inner screw rests on the upper end surface 41a, 41b of the pressure element, a flow of the material of the elastic rod 9 when the projections 12, 39 press on the rod does not lead to a loosening of the fixation of the head 22 in the receiving part 25.

As the locking of the rod is achieved by pressing the projections 39, 12 into the surface of the rod without harming the integral structure of the rod secondary adjustments are possible.

Modifications of the above described embodiments are possible.

The number of the rib-like projections may vary. Instead of having only rib-like projections provided at the surface of the locking element and the seat a combination of projections and depressions can be provided. Hence, this allows the material which is displaced when the projections press onto the surface of the rod to flow in the depressions to generate a form-fit connection. Additionally, the volumes of projections and depressions can be similar or have the same size such that after the flow of material is completed, the volume of the rod in a region of the connection with the receiving part has approximately the same size as before.

The projections and/or depressions need not to have a rib-like or groove-like structure but can have any shape. The projection which comes into contact with the surface of the rod can have another shape than a ring shape. Depending on the external load, at least one tooth should be provided which can be shaped so as to sink into the surface of the rod to create an indirect form-fit between the locking element and the rod or between the seat and the rod, respectively. A ring-shaped structure of the projection on the locking element is preferable, since it facilitates tightening of the locking element by means of a turning motion.

The rod needs not to have a circular cross section. It can have an oval rectangular or square cross section.

The second embodiment, to avoid a flowing out of material through the bore 40 provided in the pressure element, a cap can be provided for closing the bore after the bone anchoring element is screwed into the bone.

The locking element can also be modified. For example, the locking element can be a nut with a coaxial pin which is formed in one piece with the nut. The pin has the projection which comes into contact with the surface of the rod. In this case, the free legs of the receiving part have an external thread which cooperates with the thread of the nut. In the second embodiment described above the bone anchoring element is introduced from the top into the receiving part. However, the bone anchoring element can also be introduces from the bottom of the receiving part if the receiving part is constructed to allow this.

The head of the bone anchoring element and the shaft can be constructed as separate parts which can be assembled.

The invention is not limited to screws as bone anchoring elements but can be realized with bone hooks or any other bone anchoring element.

What is claimed is:

1. A bone anchoring device comprising
an anchoring element comprising a shank to be anchored in a bone or a vertebrae;
a connection element having a longitudinal axis for connecting at least two anchoring elements, the connection element being made of an elastic material;
a receiving part being connected to the shank for receiving the connection element and for connecting the connection element to the shank;
a seat for the connection element, the seat being provided in the receiving part;
a one piece monolithic locking element being rotatably engageable with the receiving part for fixation of the connection element in the seat;
wherein at least a portion of the connection element that is to be received in the seat has a constant cross-section along the longitudinal axis and wherein the locking element has an engagement structure that is configured to contact the portion of the connection element when the portion of the connection element is seated in the seat and the locking element is rotatably engaged with the receiving part, and
wherein when the portion of the connection element is fixed in the seat upon tightening of the locking element, the elastic material is configured to flow for a form-fit connection between the connection element and the engagement structure of the locking element;
wherein the seat comprises an engagement structure that is configured to contact the portion of the connection element when the portion of the connection element is seated in the seat and the locking element is rotatably engaged with the receiving part;
wherein the engagement structure of the seat comprises an elongate projection which length extends in a direction transverse to the longitudinal axis of the connection element;
wherein the receiving part has a substantially U-shaped recess forming two open legs with an inner thread provided on the legs and wherein the locking element is an inner screw to be screwed-in between the legs;
wherein the engagement structure of the locking element is a ring-shaped projection; and,
wherein a diameter of the ring-shaped projection equals a distance between two elongate projections of the seat.

2. A bone anchoring device comprising
an anchoring element comprising a shank to be anchored in a bone or a vertebrae;
a connection element having a longitudinal axis for connecting at least two anchoring elements, the connection element being made of an elastic material;
a receiving part being connected to the shank for receiving the connection element and for connecting the connection element to the shank;
a seat for the connection element, the seat being provided in the receiving part; a one piece monolithic locking element being rotatably engageable with the receiving part for fixation of the connection element in the seat;
wherein at least a portion of the connection element that is to be received in the seat has a constant cross-section along the longitudinal axis and wherein the locking element has an engagement structure that is configured to contact the portion of the connection element when the portion of the connection element is seated in the seat and the locking element is rotatably engaged with the receiving part, and wherein when the portion of the connection element is being fixed in the seat upon tightening of the locking element, the elastic material is configured to flow for a form-fit connection between the connection element and the engagement structure of the locking element;

wherein the seat comprises an engagement structure that is configured to contact the portion of the connection element when the portion of the connection element is seated in the seat and the locking element is rotatably engaged with the receiving part;

wherein the engagement structure of the seat comprises an elongate projection which length extends in a direction transverse to the longitudinal axis of the connection element.

3. The bone anchoring device according to claim 1, wherein the receiving part has a substantially U-shaped recess forming two open legs with an inner thread provided on the legs and wherein the locking element is an inner screw to be screwed-in between the legs.

4. The bone anchoring device according to claim 3, wherein the engagement structure of the locking element is a ring-shaped projection.

5. The bone anchoring device according to claim 2, wherein the engagement structures of the locking element and the seat comprise projections.

6. The bone anchoring device according to claim 2, wherein the engagement structure of any one of the locking element and the seat comprises depressions.

7. The bone anchoring device of claim 2, wherein the receiving part has a substantially U-shaped recess forming two open legs and wherein the seat is provided at the bottom of the recess.

8. The bone anchoring device of claim 2, wherein the bone anchoring element is pivotably connected to the receiving part and wherein the seat is provided in a pressure element which is movable in the receiving part and locks the angular position of the bone anchoring element if pressure is exerted on the pressure element.

9. The bone anchoring device according to claim 2, wherein the connection element is made of an elastomer material.

10. The bone anchoring device according to claim 2, wherein the connection element is a rod.

11. The bone anchoring device according to claim 2, wherein the surface of the portion of the connection element is a substantially smooth surface without any one of projections and depressions.

12. The bone anchoring device according to claim 2, wherein the engagement structure of the locking element engages the surface of the connection element to create an indirect form-fit connection.

13. The bone anchoring device according to claim 2, wherein the engagement structure of the seat engages the surface of the connection element to create an indirect form-fit connection.

14. The bone anchoring device according to claim 2, wherein the locking of the connection element in the receiving part is achieved by a frictional connection with a portion of an indirect form-fit connection of the locking element with the connection element.

15. The bone anchoring device of claim 2, wherein the connection between the locking element and the receiving part is a threaded connection.

16. The bone anchoring device of claim 2, wherein the rod is clamped between the seat and the locking element and wherein a contour of the seat and a contour of the locking element deviate from the contour of the rod.

17. The bone anchoring device of claim 2, wherein the elongate projection of the engagement structure of the seat substantially forms a U-shape.

18. The bone anchoring device of claim 2, wherein the form-fit connection between the connection element and the engagement structure of the locking element occurs without harming the integrity of a surface of the connection element.

19. A method of attaching a bone anchoring device to a bone or vertebrae, the bone anchoring device comprising;
    an anchoring element comprising a shank to be anchored in a bone or a vertebrae;
    a connection element having a longitudinal axis for connecting at least two anchoring elements, the connection element being made of an elastic material;
    a receiving part being connected to the shank for receiving the connection element and for connecting the connection element to the shank;
    a seat for the connection element, the seat being provided in the receiving part;
    a one piece monolithic locking element being rotatably engageable with the receiving part for fixation of the connection element in the seat;
    wherein at least a portion of the connection element that is to be received in the seat has a constant cross-section along the longitudinal axis and wherein the locking element has an engagement structure that is configured to contact the portion of the connection element when the portion of the connection element is seated in the seat and the locking element is rotatably engaged with the receiving part, and
    wherein when the portion of the connection element is fixed in the seat upon tightening of the locking element, the elastic material is configured to flow for a form-fit connection between the connection element and the engagement structure of the locking element;
    wherein the seat comprises an engagement structure that is configured to contact the portion of the connection element when the portion of the connection element is seated in the seat and the locking element is rotatably engaged with the receiving part;
    wherein the engagement structure of the seat comprises an elongate projection which length extends in a direction transverse to the longitudinal axis of the connection element;
  the method comprising:
    attaching the anchoring element to a bone or vertebrae;
    connecting the connection element to the receiving part connected to the anchoring element;
    fixing the connection element in the seat with the locking element, the fixing comprising the engagement structure of the locking element contacting the portion of the connection element, wherein when the connection element is fixed in the seat upon tightening of the locking element, the elastic material flows for a form-fit connection between the connection element and the engagement structure of the locking element.

20. The method of claim 19, wherein fixing the connection element in the seat further comprises having a substantially smooth surface of the connection element contacting the engagement structure of the seat.

21. The method of claim 19, wherein fixing the connection element in the seat comprises screwing an outer thread of the locking element into an inner thread provided on legs of the receiving part defined by a U-shaped recess of the receiving part.

\* \* \* \* \*

UNITED STATES PATENT AND TRADEMARK OFFICE
CERTIFICATE OF CORRECTION

| | | |
|---|---|---|
| PATENT NO. | : 8,568,458 B2 | Page 1 of 1 |
| APPLICATION NO. | : 11/854508 | |
| DATED | : October 29, 2013 | |
| INVENTOR(S) | : Matthis et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1262 days.

Signed and Sealed this
Seventeenth Day of February, 2015

Michelle K. Lee
*Deputy Director of the United States Patent and Trademark Office*